United States Patent [19]

Isono

[11] Patent Number: 4,560,382
[45] Date of Patent: Dec. 24, 1985

[54] MEDICAL CONTAINER

[75] Inventor: Keinosuke Isono, Kawaguchi, Japan

[73] Assignee: Terumo Corporation, Tokyo, Japan

[21] Appl. No.: 596,537

[22] Filed: Apr. 4, 1984

[30] Foreign Application Priority Data

Aug. 15, 1983 [JP] Japan ................. 58-149019

[51] Int. Cl.⁴ .............................................. A61B 5/00
[52] U.S. Cl. ................................................... 604/408
[58] Field of Search ............... 604/408, 320, 403, 322, 604/406; 210/927

[56] References Cited

U.S. PATENT DOCUMENTS 3,828,779  8/1974  Ogle .
3,945,382  3/1976  Ogle .
4,201,207  5/1980  Buckles et al. .
4,437,472  3/1984  Naffulin .............................. 604/408

FOREIGN PATENT DOCUMENTS 894715  1/1983  Belgium .
1587522  4/1981  United Kingdom .

Primary Examiner—John D. Yasko
Assistant Examiner—Christa K. Scott
Attorney, Agent, or Firm—Frishauf, Holtz, Goodman & Woodward

[57] ABSTRACT

In a medical container comprising a flexible vessel containing a fluid, inlet means attached to the vessel for admitting another fluid into the vessel, and an outlet, a tubular member is extended through the vessel wall as the inlet means and closed at the outer end with a plugging member to shut off the tubular member channel from the exterior and provided at the inner end with a bacterial filter, the plugging member permitting access to the tubular member channel from the exterior when the other fluid is to be admitted into the vessel. A breakable closure member is further mounted on the inner end of the tubular member to shut off the filter member from the interior space of the vessel, but is breakable to permit the communication of the interior space with the tubular member when the other fluid is to be admitted.

24 Claims, 6 Drawing Figures

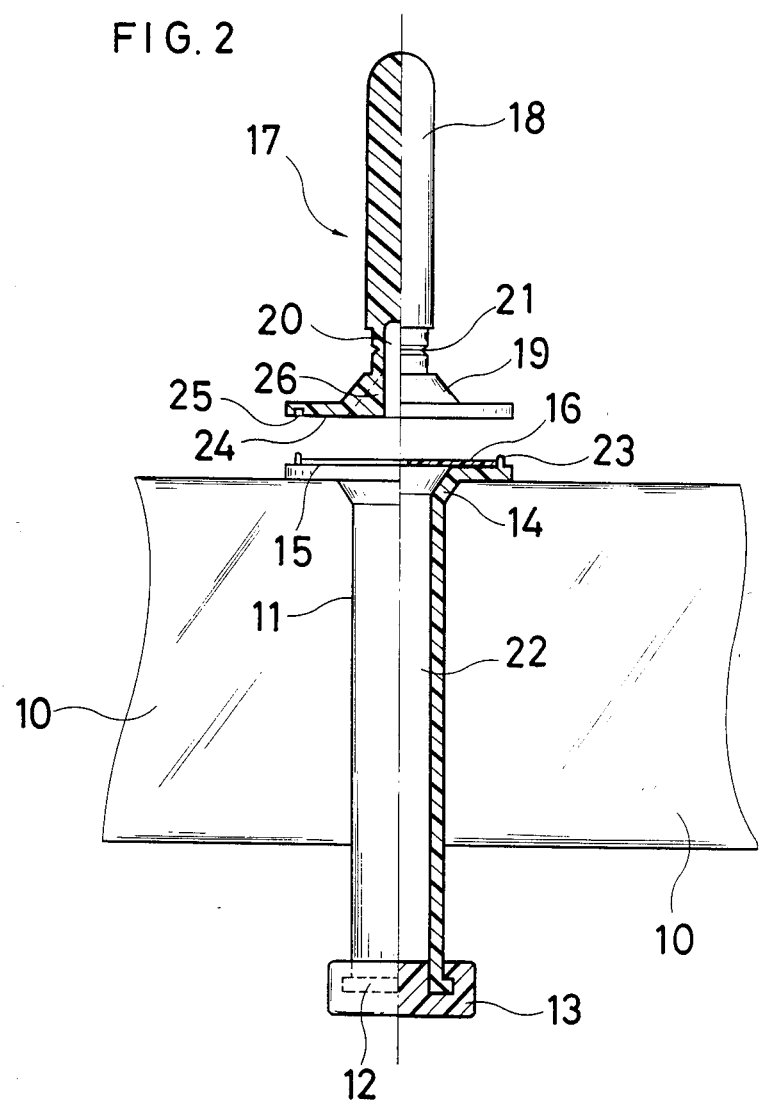

MEDICAL CONTAINER

BACKGROUND OF THE INVENTION

1. Field of the Invention

The present invention relates to a medical container, and more particularly, to the structure of an inlet attached to a medical container for admitting an additional medication to a fluid contained in the container.

2. Description of the Prior Art

The following types of treatment for chronic renal failure have been developed as alternatives to prolonged dialysis.

(1) Intermittent Peritoneal dialysis (IPD)

IPD, essentially lavage of the peritoneal membrane, is a method of dialysis that utilizes the peritoneal membrane as the dialysis membrane. A predetermined volume (1500–2000 ml) of dialysate is instilled via a catheter into the peritoneal cavity from a bag containing the dialysate. There it is held for 30 to 60 minutes to allow dialysis to occur, following which it is drained from the peritoneal cavity. Dialysis is carried out by repeating this process anywhere from a few times to several dozen times.

(2) Continuous Ambulatory Peritoneal dialysis (CAPD)

In CAPD, about 2000 ml of dialysate is instilled into the peritoneal cavity from a dialysate bag, and four exchanges are carried out daily. This method does not impose the physical restrictions of prolonged dialysis therapy, and is well suited for helping the patient resume normal activities. Because dialysis is carried out continuously, CAPD approaches the natural kidney function and is also excellent for the body.

(3) CCPD

CCPD is a form of therapy midway between CAPD and IPD. Multiple dialysate bags are connected to a catheter via valves, and the exchange of dialysate between the bag and the peritoneal cavity is carried out by manipulating the valves. CCPD is carried out daily, and differs from IPD in that the amount of fluid used per exchange is smaller.

Dialysis bags are used in these types of therapy, and when there are other indications such as diabetic nephropathy, insulin must be added as required to the dialysate in the bag. For this reason, it is desirable that dialysis bags be provided with a medication inlet, and in fact such inlets are always provided on bags in current CAPD systems.

However, this medication inlet and the process of admitting medication can become one of the causes of bacterial infection, which is the single greatest problem with this type of therapy. In peritoneal dialysis, there exists a risk of peritonitis due to bacterial contamination. In these types of therapy in particular, the addition process is often carried out by the patient himself rather than a specialist. Hence, the medication inlet should be so constructed as to prevent bacterial contamination. In existing systems of the above type, however, nothing whatsoever has been done to prevent bacterial infection via the medication inlet.

SUMMARY OF THE INVENTION

An object of the present invention is, therefore, to provide a medical container having a medication inlet capable of minimizing the likelihood of bacterial infection during the addition of medication and facilitating the addition process.

The present invention is directed to a medical container comprising a flexible vessel defining an interior space for containing a fluid, at least one inlet means provided across the wall of the vessel for admitting another fluid into the interior space for admixing, and outlet means for transferring the fluid out of the vessel. According to a first aspect of the present invention, the inlet means comprises a tubular member extending through the vessel wall and defining a channel in communication with the interior space. Plugging means is mounted on the tubular member for shutting off the channel in the tubular member from the exterior, and a bacterial filter member is attached to the tubular member on the side of the interior space with respect to the plugging means. The plugging means is able to permit access to the tubular member channel from the exterior when the other fluid is to be admitted into the interior space of the vessel.

According to a second aspect of the present invention, closure means is further mounted on the tubular member on the side of the interior space with respect to the filter member for shutting off the filter member from the interior space. The closure means is breakable to permit the communication of the interior space with the filter member when the other fluid is to be admitted into the interior space.

BRIEF DESCRIPTION OF THE DRAWINGS

The above and other objects, features and advantages of the invention will be more fully understood by reading the following description when taken in conjunction with the accompanying drawings, in which:

FIG. 2 is an elevational, partially cross-sectional, view of a first embodiment of the inlet means of the medical container of the present invention;

DESCRIPTION OF THE PREFERRED EMBODIMENTS

Although a peritoneal dialysis bag is described herein as a typical example of the medical container, this in no way limits the scope of the present invention. The present invention is equally applicable to blood bags, I.V. solution bags, urinary drainage bags, and other containers having medication inlets.

Figure 1:
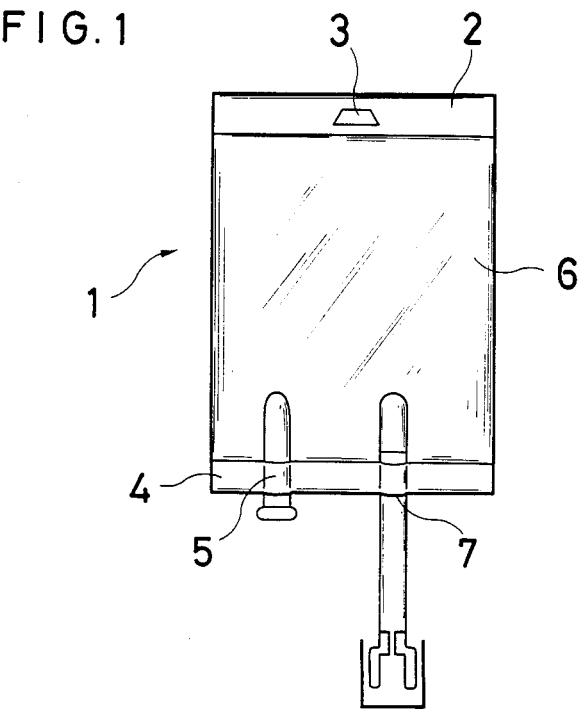
FIG. 1 is a side view of a dialysis bag.

FIG. 1 shows the standard construction of a dialysis bag 1 comprising a flexible vessel defining an interior space 6 and having upper and lower portions 2 and 4 sealed. A hanger hole 3 is formed in the upper sealed portion 2. In the lower sealed portion 4 are provided an inlet 5 for admitting an additional medication as required, for example, antibiotics, heparin, insulin, and the like, and an outlet 7 that is to be connected to a Tenckhoff catheter, puncture needle or the like and used when solution within the interior space 6 of the bag 1 is transferred out.

As has already been noted above, there are problems with this type of addition inlet structure. The present invention has resolved the difficulties that have hitherto arisen with the addition inlets of medical containers.

FIG. 2 shows an addition inlet construction in a first embodiment of the medical container of the present invention. A tubular member 11 extends through a sealed wall 10 of the vessel of the medical container, and thus communicates the interior space containing the fluid with the container exterior. The tubular member 11 has an open outer end extending out of the wall and formed with a flange 12 on which a rubber cap 13 is tightly fitted. The rubber cap 13 can be punctured with a hypodermic needle when medication is to be admitted. The tubular member 11 has an inner end 14 which is flared toward the interior space. On the surface 15 of the flared end 14 a bacterial filter member 16 is attached and held in place by downwards pressure applied by a breakable closure member 17. An injection channel 22 is defined in the tubular member 11 between the filter member 16 and the rubber cap 13.

The breakable closure member 17 consists of an upper cylindrical (rigid) portion 18 and a flared base 19, and includes at the center thereof a cavity 20 that extends from the flared base 19 to the cylindrical portion 18. At a point on the outer periphery of the cylindrical portion 18 overlying this cavity 20 is formed a circumferential notch 21 that permits the cylindrical portion 18 to be broken off when necessary to provide fluid communication between the interior space within the vessel and the injection channel 22 of the tubular member 11.

A rib 23 is circumferentially formed on the surface 15 of the flared inner end 14 of the tubular member 11. A matching groove 25 is circumferentially formed in the surface 24 of the flared base 19 of the breakable closure member 17. The filter member 16 is interposed between the surface 15 of the flared inner end 14 of tubular member 11 and the surface 24 of the flared base 19 of closure member 17, and secured in a heat seal manner by the mating engagement between rib 23 and groove 25.

Figure 3:
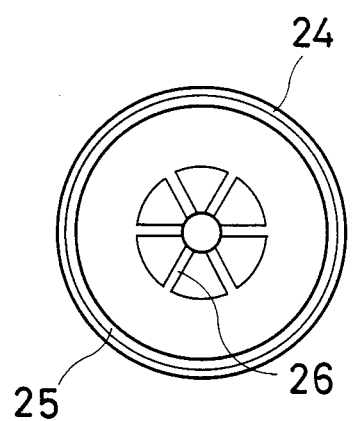
FIG. 3 is a bottom view of the breakable closure member.

The pores in the filter member 16 may preferably have a size of less than 0.45 $\mu$m to prevent the passage of a bacterium, *Serratia marcescens*, and more preferably less than 0.2 $\mu$m to prevent the passage of *Pseudomonas diminuta*. The filter member 16 having such submicron pores is not properly supported merely by attachment of its periphery, and may be damaged during the addition of medication or at other times. Accordingly, as shown in FIG. 3, radial arms 26 are formed in the surface 24 of the flared base 19 of the closure member 17, thereby supporting the filter member 16 over its full surface. Instead of being supported by just one part of the closure member 17, the filter member 16 may also be supported by other parts as well.

In this type of construction, the breakable closure member 17 prevents the filter member 16 from being continuously immersed in solution. This is safe because it eliminates the elution of chemical components of the filter member 16. Moreover, with this construction, the outer end of tubular member 11 may be provided with a Luer connector structure, not shown in the figure, rather than the rubber cap 13 tightly fitted thereon.

The Luer connector structure may consist of a tapered female portion provided on the outer end of tubular member 11 and a plug with a tapered male portion that fits therein. More preferably, fastening means such as a screw thread may be formed on the periphery of the tapered female portion to firmly secure the plug. At the time of addition, the plug is removed, the tip portion of a syringe holding the medication to be added is engaged with the tapered female portion, allowing the medication to be admitted into the interior space. Once addition is over, the plug should be fitted in the tapered female portion to restore fluid tightness.

Figure 4:
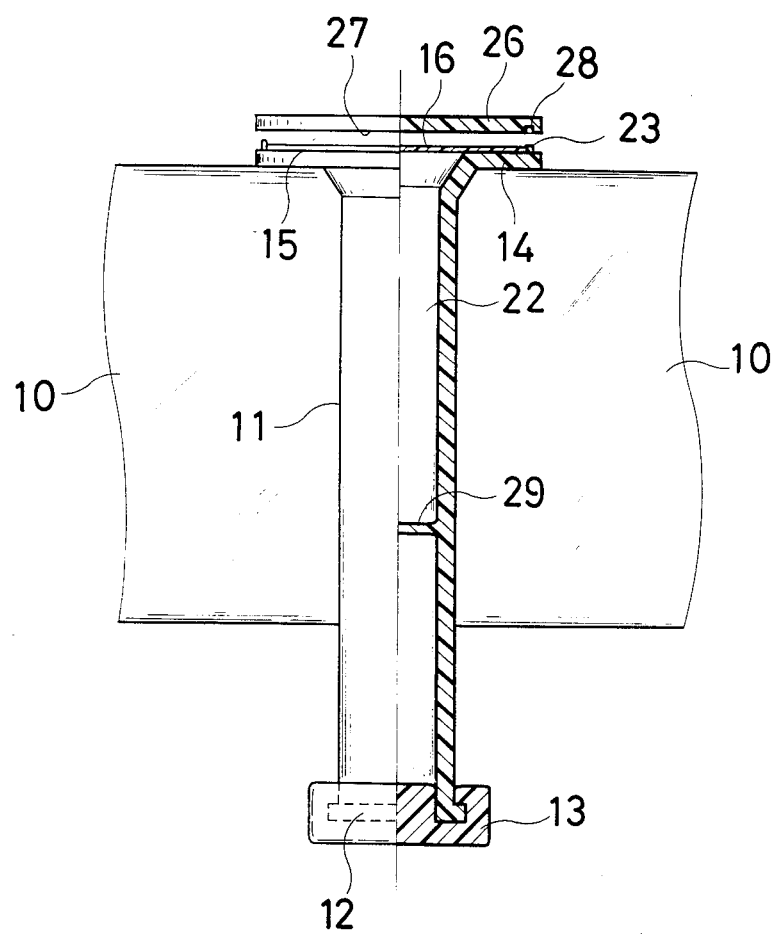
FIG. 4 is an elevational, partially cross-sectional, view of a second embodiment of the inlet means of the medical container according to the present invention.

FIG. 4 shows an addition inlet construction according to a second embodiment of the medical container of the present invention. The first example shown in FIG. 2 and the second example shown in FIG. 4 fulfill substantially the same objects and functions. Their structural differences are as follows. In the second example, instead of attaching the breakable closure member 17 to the inner end 15 of tubular member 11, a disc-shaped support 26 for the filter member 16 is attached by engaging a groove 28 in the lower surface 27 thereof with the rib 23 on the flared inner end 14 of tubular member 11. The support 26 is preferably welded to the surface 15 of the flared end 14, thereby securing the filter member in place. In addition, an intermediate partition 29 traverses the tubular member 11 between the filter member 16 and the outer end of the tubular member 11, preventing the solution from reaching the rubber cap 13. Although not shown, this intermediate partition 29 may also be provided in the first example of the addition inlet structure.

A medication injection channel is thus defined between filter member 16 and intermediate partition 29. The material and location of the partition 29 must be selected such that it may be punctured with a hypodermic needle inserted through the cap 13 from the exterior. The partition 29 must also be made to such a thickness as to be puncturable with a hypodermic needle during addition, but not rupturable under the presssure applied during autoclave sterilization.

Figure 5:
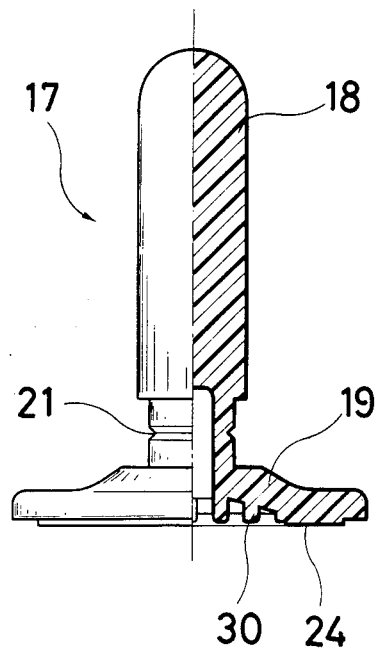
FIG. 5 is an elevational, partially cross-sectional, view of another example of the breakable closure member.
Figure 6:
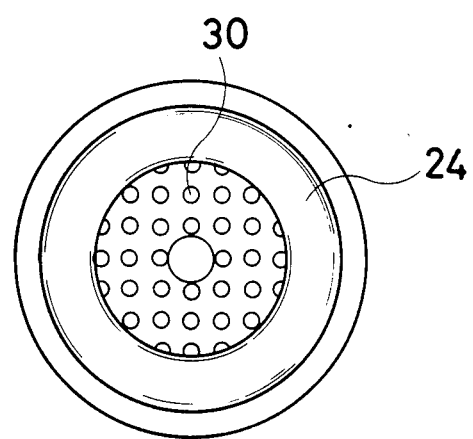
FIG. 6 is a bottom view of the closure member of FIG. 5.

As described with reference to FIG. 3, the support 26 may take the form of radial arms to uniformly support the filter member 16. A more preferred example of the support means is illustrated in FIGS. 5 and 6. A plurality of spaced-apart studs 30 extend from the tapered surface defining the end opening of the base 19 of the breakable closure member 17. The studs 30 terminate substantially in the plane of the opening and their tips function to support the filter member. Since the filter member is supported at a plurality of points of contact, the area of contact of the filter member with the support means is minimized, preserving the effective area of the filter member.

In both examples, since the filter member 16 must not be damaged by the hypodermic needle and the like during addition, a suitable spacer (not shown) may be inserted in the injection channel 22.

It will be understood that the inner end 14 of the tubular member 11 and the base 19 of the closure member 17 are flared or tapered because the dead space for fluid is then reduced to enable maximum utilization of the fluid. Fluid will be undesirably retained otherwise, for example, in a rectangular recess.

The addition process is described below for the medical container of the present invention.

In the first example shown in FIG. 2, tubular member 11 is held in one hand, and breakable closure member 17 in the other. Member 17 is broken at notch 21 by bending, bringing the solution in the container in communication with channel 22 in tubular body 11. If the outer end of tubular member 11 is closed with rubber cap 13, the needle of a syringe filled with the medication to be added is passed through rubber cap 13 without damaging filter member 16, and the medication is injected into channel 22 and then to interior space 6. The injected medication is admixed with the solution within the vessel and provided for fluid transfer while being filtered free of bacteria by means of filter member 16.

When the outer end of tubular member 11 has a Luer connector, the plug is removed at the time of addition. The front tip portion of a syringe holding the medication to be added is engaged with the tapered female portion and the medication added. When addition is complete, the plug should be returned to the tapered female portion to restore fluid tightness.

In the second example shown in FIG. 4, the needle on a syringe filled with the medication to be added is passed through rubber cap 13 and intermediate partition 29 without damaging filter member 16, and the medication is injected into channel 22. Following this the procedure is identical to that described in conjunction with the first example. It is to be noted that rubber cap 13 with a suitable compliance can effectively prevent fluid leakage.

Examples of medical containers to which the present invention applies other than the dialysate-containing bags for CAPD therapy described above include blood bags containing blood preservatives, I.V. solution bags containing I.V. solutions, and urinary drainage bags. Each of these should preferably be sterilized in an autoclave prior to being made commercially available.

The addition inlet means of the medical container of the present invention has many advantages, as described below.

(1) It prevents the entry of bacteria into the solution within the container during the addition of medication. This makes it possible in dialysis bags to prevent the possibility of peritonitis and the like from arising by minimizing the risk of infection by bacteria, which is the single largest problem with the use of CAPD and IPD systems.

(2) The addition process is easy, and can be safely carried out by the patient himself, without the help of a specialist.

(3) It facilitates the treatment of diabetic nephropathy.

(4) In the first embodiment in which a breakable closure member is attached on the interior side of the filter member, the filter member does not come into contact with solution until the time of use. Not only the physical properties of the filter do not change, but there is no entry of leachates from the filter into the solution, making it possible to protect the filter when subjected to a rise in internal pressure during autoclave sterilization.

(5) In the second embodiment in which the breakable closure member is omitted, the space between the plugging means or cap and the filter is filled with solution, which prevents the entry of air in the filter pores. Moreover, air does not enter during the addition of medication either, thus preventing blocking of the filter by air and permitting effective utilization of the filter surface area. If an intermediate partition puncturable with a needle is provided between the filter member and the outer end of the tubular member in this second embodiment, the fluid does not come in contact with the rubber cap until the time of use, obviating the risk of contaminating the fluid with leachates from the cap.

What is claimed is:

1. A medical container comprising a flexible vessel defining an interior space for containing a fluid, at least one inlet means provided across the wall of said vessel for admitting another fluid into the interior space for admixing, and outlet means for transferring the fluid out of the interior space, characterized in that said inlet means comprises a tubular member extending through the vessel wall and defining a channel in communication with said interior space, plugging means mounted on said tubular member for shutting off the channel in said tubular member from the exterior, and for permitting access to the tubular member channel from the exterior, a bacterial filter member traversing said tubular member on the side of the interior space with respect to said plugging means, and closure means mounted on said tubular member on the side of said interior space with respect to said filter member for shutting off said filter member from said interior space, and for permitting communication of said interior space with said filter member when the other fluid is to be admitted into said interior space.

2. The medical container according to claim 1 wherein said closure means is at least partially breakable to permit said communication of the interior space of the vessel with said filter member when the other fluid is to be admitted into the interior space.

3. The medical container according to claim 2 wherein said tubular member has an open inner end in communication with said interior space and an open outer end in communication with the exterior, said plugging means is mounted on the outer end of said tubular member, and said bacterial filter member is attached to the inner end of said tubular member.

4. The medical container according to claim 3 wherein said closure means comprises a cylindrical member having open and closed ends, the open end of said cylindrical member is mated with the inner end of said tubular member with said filter member interposed therebetween, and said cylindrical member is breakable at an intermediate position.

5. The medical container according to claim 4 wherein said cylindrical member comprises a circumferential notch at an intermediate position for breakage.

6. The medical container according to claim 3, wherein the inner end of said tubular member is flared toward the interior space.

7. The medical container according to claim 4 wherein the open end of said cylindrical member is provided with means for supporting said filter member.

8. The medical container according to claim 7 wherein said supporting means comprises radial arms.

9. The medical container according to claim 7 wherein said supporting means comprises a plurality of axially extending studs having tips in the plane of the open end of said cylindrical member.

10. The medical container according to claim 1, wherein said plugging means is formed of an elastic material puncturable with a puncture needle.

11. The medical container according to claim 10 wherein said plugging means is a rubber cap.

12. The medical container according to claim 3 wherein said plugging means is a plug removably fitted on the outer end of said tubular member.

13. A medical container comprising a flexible vessel defining an interior space for containing a fluid, at least one inlet means provided across the wall of said vessel for admitting another fluid into the interior space for admixing, and outlet means for transferring the fluid out of the interior space, characterized in that said inlet means comprises a tubular member extending through the vessel wall and defining a channel in communication with said interior space, plugging means mounted on said tubular member for shutting off the channel in said tubular member from the exterior, but being able to bring them in communication when the other fluid is to be admitted into said interior space, and a bacterial filter member traversing said tubular member on the side of the interior space with respect to said plugging means.

14. The medical container according to claim 13 wherein said tubular member has an open inner end in communication with said interior space and an open outer end in communication with the exterior, said plugging means is mounted on the outer end of said tubular member, and said bacterial filter member is attached to the inner end of said tubular member.

15. The medical container according to claim 14 which further comprises a puncturable partition traversing said tubular member at an intermediate position between its inner and outer ends.

16. The medical container according to claim 13 wherein said plugging means is formed of an elastic material puncturable with a puncture needle.

17. The medical container according to claim 15 wherein said plugging means is a rubber cap.

18. The medical container according to claim 13 wherein said plugging means is a plug removably fitted on the outer end of said tubular member.

19. The medical container according to claim 14 wherein the inner end of said tubular member is flared toward the interior space.

20. The medical container according to claim 4, wherein the inner end of said tubular member is flared toward the interior space.

21. The medical container according to claim 2, wherein said plugging means is formed of an elastic material puncturable with a puncture needle.

22. The medical container according to claim 21, wherein said plugging means is a rubber cap.

23. The medical container according to claim 3, wherein said plugging means is formed of an elastic material puncturable with a puncture needle.

24. The medical container according to claim 23, wherein said plugging means is a rubber cap.

* * * * *